(12) United States Patent
Rehm

(10) Patent No.: US 8,348,984 B2
(45) Date of Patent: Jan. 8, 2013

(54) METHOD AND APPARATUS FOR SURGICAL CLAMPING

(75) Inventor: Walter Rehm, Tuttlingen (DE)

(73) Assignee: Max Hauster Süeddeutsche Chirurgiemechanik GmbH, Tuttlingen (DE)

(*) Notice: Subject to any disclaimer, the term of this patent is extended or adjusted under 35 U.S.C. 154(b) by 886 days.

(21) Appl. No.: 12/261,453

(22) Filed: Oct. 30, 2008

(65) Prior Publication Data
US 2009/0125073 A1 May 14, 2009

(30) Foreign Application Priority Data
Oct. 31, 2007 (DE) .................. 10 2007 052 315

(51) Int. Cl.
*A61B 17/84* (2006.01)
*A44B 11/25* (2006.01)
(52) U.S. Cl. ............. 606/324; 606/105; 24/459; 24/528
(58) Field of Classification Search ........... 606/86 R, 606/99, 216–221, 324, 151, 157, 57, 105; 600/241–246; 24/16 R, 16 PB, 20 TT, 459, 24/527–528, 593.11; 623/17.15, 23.47
See application file for complete search history.

(56) References Cited

U.S. PATENT DOCUMENTS

| | | | | |
|---|---|---|---|---|
| 4,201,215 A | | 5/1980 | Crossett et al. | |
| 4,730,615 A | * | 3/1988 | Sutherland et al. | 606/215 |
| 5,074,696 A | * | 12/1991 | Tanaka | 402/52 |
| 5,439,463 A | * | 8/1995 | Lin | 606/252 |
| 5,928,231 A | * | 7/1999 | Klein et al. | 606/60 |
| 6,051,007 A | * | 4/2000 | Hogendijk et al. | 606/151 |
| 6,704,972 B2 | * | 3/2004 | Pyle | 24/16 PB |
| 7,361,179 B2 | * | 4/2008 | Rousseau et al. | 606/281 |
| 2005/0240189 A1 | * | 10/2005 | Rousseau et al. | 606/72 |
| 2006/0195101 A1 | | 8/2006 | Stevens et al. | |

FOREIGN PATENT DOCUMENTS

| | | |
|---|---|---|
| DE | 1611924 | 3/1971 |
| DE | 8222027 | 11/1982 |

OTHER PUBLICATIONS

Albee, Fred H. Bone surgery with Machine Tools. Scientific American. Apr. 1936, vol. 154, No. 4, pp. 178-181.*
German Office Action dated Jul. 12, 2010, Appln. Serial No. 10 2007 052 315.9-35, 7 pages (with English translation).

* cited by examiner

*Primary Examiner* — Kevin T Truong
*Assistant Examiner* — Larry E Waggle, Jr.
(74) *Attorney, Agent, or Firm* — Andrew F. Young, Esq.; Lackenbach Siegel, LLP

(57) ABSTRACT

The invention concerns a clamp, especially a surgical clamp, with a left clamp half to receive a left half of a breastbone during a surgical procedure, a right clamp half to receive a right half of the breastbone, as well as a first toothed rod and a detent mechanism engaging in the first toothed rod to secure the left clamp half at a distance from the right clamp half, wherein the detent mechanism engaging in the first toothed rod has a detent region extending at least from the left clamp half to the right clamp half.

24 Claims, 4 Drawing Sheets

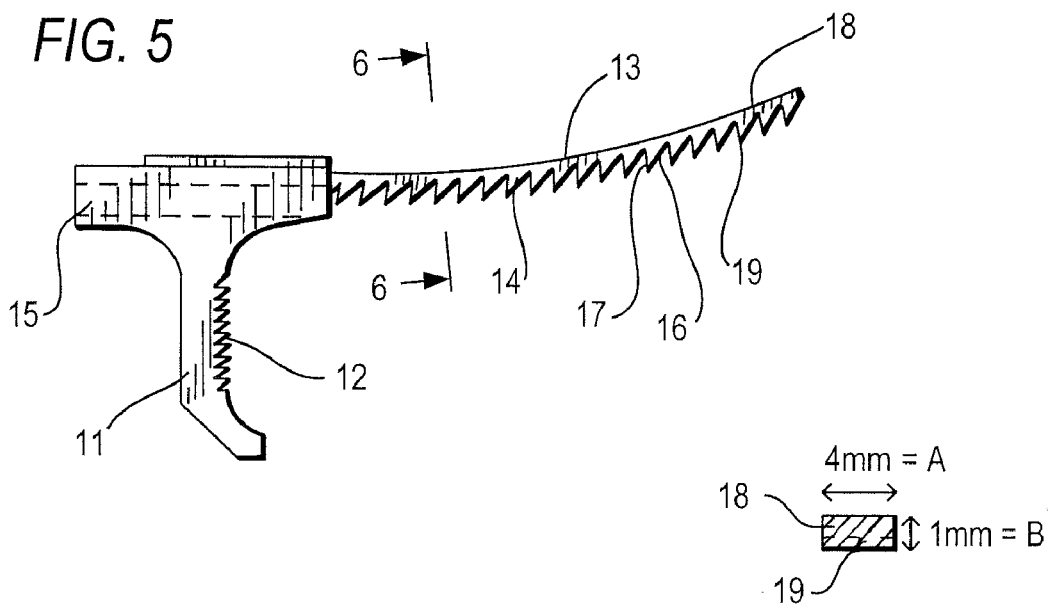
FIG. 5
FIG. 6
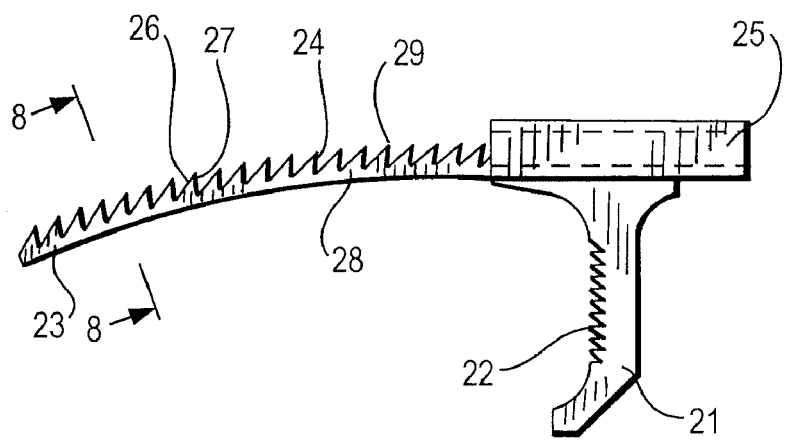
FIG. 7
FIG. 8

METHOD AND APPARATUS FOR SURGICAL CLAMPING

CROSS REFERENCE TO RELATED APPLICATIONS

This application relates to and claims priority from DE 10 2007 052 315.9, filed Oct. 31, 2007, the entire contents of which are herein incorporated fully by reference.

FIGURE SELECTED FOR PUBLICATION

FIG. 3.

BACKGROUND OF THE INVENTION

1. Field of the Invention

The present invention relates to a clamp. More specifically, the present invention relates to a surgical breastbone clamp containing a detent mechanism extending between respective opposing clamp halves.

2. Description of the Related Art

The related art involves the performing of medical operations on the open rib cage, such as heart operations. These operations have almost become a routine procedure, one which is often done. In order to open the rib cage, one generally saws the breastbone (sternum) lengthwise, making it possible to spread the ribs apart and work freely in/on the open chest.

After the operation, the chest has to be closed again. In particular, one must create the conditions for the lengthwise separated breastbone to heal once more, which necessarily requires, among other things, a fixation of the two halves of the breastbone in a defined position to each other. A number of techniques are known for this. As a rule, the connecting of the two halves of the sternum is done with surgical thread or by tacking together. However, in a number of problem patients, such as those with a strong chronic cough, there are complications due to the fact that the thread is exposed to strong stress and will break.

More stable alternative techniques, but still not used as standard methods today, are the applying of perforated strips on/in the bone and screwing them together, or the joining and fixing of the halves of the breastbone with a massive clamp.

Among these techniques, one preferred technique uses a generally two-part clamp with two clamp halves, each of which grasps one outer side of a breastbone half. The two halves of the clamp are than moved toward each other until the halves of the breastbone are pressed against each other with the desired pressure and fixed in this position. The advantage with the use of such clamps is that, besides the high-strength connection of the sternum halves which it accomplishes, no further procedures are required for the breastbone, such as making of holes to lead a thread through, applying of perforated strips, or forcing of wire staples into the breastbone with a tacker device.

Clamps which are used for the joining and fixing of the breastbone are known, for example, from DE 8222027, U.S. Pat. No. 6,051,007 or US 2006/0195101 A1. In all of these configurations, the first half of the clamp commonly has an elongated staple-like structure with surface structurization, while the second half of the clamp has a sleeve, which is fitted onto the staple-like structure and is fixed there generally by means of a detent mechanism, provided in or on the sleeve and engaging with the surface structurization, as the two halves of the clamp are moved together into the desired end position.

However, all these clamps have a number of disadvantages in common: it is not possible to achieve a symmetrical and especially a flat bearing surface of the clamp with them. Thus, the primary effect achievable with a clamp, that of a two-dimensional pressure, as opposed to the uni-dimensional pressing of a thread, is thwarted in that the effective bearing surface is ultimately confined to the region of the sleeve. In another common disadvantage, the fixation mechanism only acts locally in a small region of the clamp and is therefore still always exposed to a certain degree of wobbling and tilting and does not achieve the highest conceivable stability. As a third common disadvantage, when tightening the clamp, it is a problem that the relative movement of the halves of the clamp toward each other still occurs only by the movement of one half of the clamp, and so the tightening is necessarily asymmetrical, which can result in a fourth common disadvantage, namely the halves of the breastbone not being fixed in the optimal position relative to each other.

Accordingly, there is a need for an improved surgical clamp that overcomes the drawbacks noted above.

SUMMARY OF THE INVENTION

An aspect of the present invention is to provide an improved surgical clamp.

The inventors have now recognized that a considerable stabilization of the locking connection can be achieved along with making the bearing surface and the stress occurring during the tightening symmetrical in that a detent mechanism is rendered symmetrical thanks to the use of two identical toothed rods.

According to an aspect of the present invention a clamp, specifically a surgical clamp is provided with a left clamp half to receive a left half of a breastbone during a surgical procedure, a right clamp half to receive a right half of the breastbone, as well as a first toothed rod and a detent mechanism engaging in the first toothed rod to secure the left clamp half at a distance from the right clamp half, wherein the detent mechanism engaging in the first toothed rod has a detent region extending at least from the left clamp half to the right clamp half.

According to another aspect of the present invention, the clamp has a left clamp half and a right clamp half, as well as a first toothed rod and a detent mechanism engaging in the first toothed rod to secure the left clamp half at a distance from the right clamp half, while the detent mechanism engaging in the first toothed rod has a detent region extending at least from the left clamp half to the right clamp half. The detent region is identified and defined broadly herein without limit as the region in which the forces are created which withstand the pulling apart of the surgical clamp.

According to another aspect of the present invention it is realized that the detent mechanism may be second toothed rod engaging in the first toothed rod during a use.

According to another aspect of the present invention, there is a particular advantage for the right clamp half and the first of the toothed rods as well as the left clamp half and the second of the toothed rods to each be a one-piece design. This configuration provides the surgeon with a system very easy to handle during a use. But a two-piece design is also possible, in which the toothed rod is shoved into the respective opening of the clamp halves from behind.

For an optimized connection of the clamp halves by means of the toothed rods, the left clamp half and the right clamp half are each provided with a housing, having a continuous opening into which at least one of the toothed rods can be introduced. This makes unnecessary any additional parts to force the locking contact between the toothed rods, which would make it more difficult to handle the clamp in practice. Preferably, the shape of the opening of the housing is adapted to the shape of the toothed rods, so that when the toothed rods have been introduced, the configuration of the housing and the opening dictates a parallel running of the toothed rods. In a two-piece design of clamp halves and corresponding toothed rods, therefore, the opening of the housing should be such that the two toothed rods can be introduced into the opening of the housing.

As an additional aspect of the present invention, an additional fixation of a clamp can be achieved, for example, for a surgical clamp, when plates with lugs are provided on the toothed rods or on the clamp halves, for screwing the surgical clamp to the bone. The lugs are advisedly arranged so that the screws can always be screwed into the bone material.

As an additional aspect of the present invention an especially good locking can be achieved when the toothing of the respective toothed rods is configured such that the flanks belonging to each tooth run in the same direction, looking from the base of the tooth to the tip of the tooth; thus, for example, both flanks run from bottom left to upper right. Thanks to this flank geometry, the two toothed rods are pulled together in the transverse direction when there is a tensile stress in the lengthwise direction. An especially advantageous aspect of the present invention is to provide a profile as a shark fin profile, since it presents an especially low resistance to the moving of the clamp halves toward each other and an especially high resistance to their moving away from each other.

As an additional aspect of the present invention, an at least partly especially intimate and thus especially effective contact between toothings is achieved by providing that at least one of the toothed rods has a curvature along its lengthwise dimension wherein the toothing is directed toward the midpoint of the curvature or away from the midpoint of the curvature. This effect is further strengthened when both toothed rods have a curvature along their lengthwise dimension, wherein the toothing is directed toward the midpoint of the curvature or away from the midpoint of the curvature and the curvatures are opposite to each other. The mutually opposing curvatures in this case can be convex or concave.

As an additional aspect of the present invention, one improvement increases the stability of the surgical clamp on the bone if the surfaces of the left clamp half and/or the right clamp half that make contact with the bone have a structurization, preferably a tooth structure.

Another aspect of the present invention provides a preferred selection of optional materials for use as the surgical clamp including: implantable steel, titanium, and high-stress plastics.

In an especially preferred embodiment of the present invention, the clamp has a housing with a length corresponding to the clamping distance of the clamp. This ensures that the ends of the toothed rods are protected and do not stick out. Thanks to this design, the clamp of the invention has the advantage that the teeth of the toothed rods are covered when the clamp is in the clamping state and thus any traumatic effect from the teeth is ruled out.

In another advantageous embodiment of the present inventive clamp, at least one of the toothed rods has a semicircular profile. When both toothed rods have a semicircular profile, a full circle cross section results in the assembled state.

The above, and other objects, features and advantages of the present invention will become apparent from the following description read in conjunction with the accompanying drawings, in which like reference numerals designate the same elements.

BRIEF DESCRIPTION OF THE DRAWINGS

FIG. 5 is a side elevated view of a left clamp half according to another exemplary embodiment wherein a curved toothed rod is provided.

FIG. 6 is a cross-sectional view along section Y-Y in FIG. 5.

FIG. 7 is a side elevated view of a right clamp half according to the second exemplary embodiment wherein a curved toothed rod is provided.

FIG. 8 is a cross-sectional view along section X-X in FIG. 7.

DETAILED DESCRIPTION OF THE PREFERRED EMBODIMENTS

Figure 1:
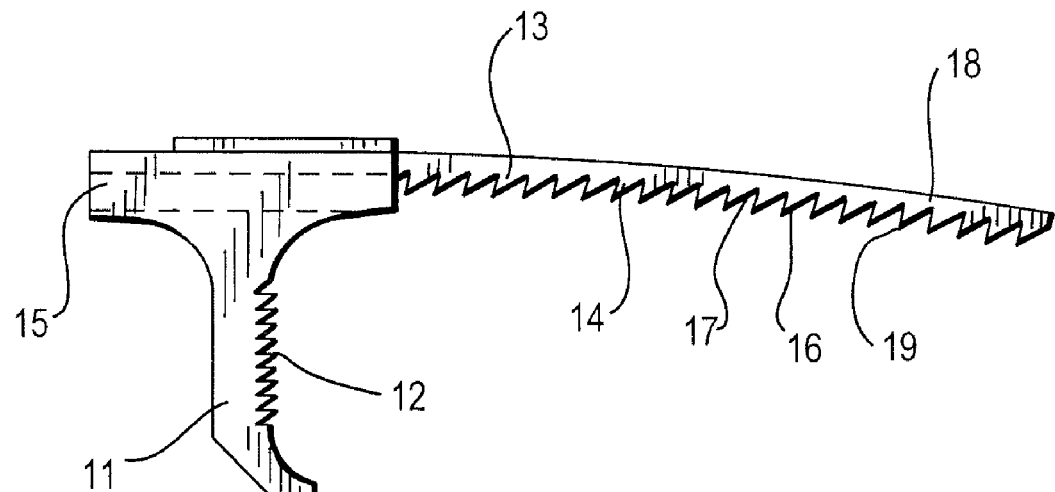
FIG. 1 is a side elevated view of a right clamp half and a first toothed rod of a clamp according to the invention.

Reference will now be made in detail to several embodiments of the invention that are illustrated in the accompanying drawings. Wherever possible, same or similar reference numerals are used in the drawings and the description to refer to the same or like parts or steps. The drawings are in simplified form and are not to precise scale. For purposes of convenience and clarity only, directional terms, such as top, bottom, up, down, over, above, and below may be used with respect to the drawings. These and similar directional terms should not be construed to limit the scope of the invention in any manner. The words "connect," "couple," and similar terms with their inflectional morphemes do not necessarily denote direct and immediate connections, but also include connections through mediate elements or devices.

FIG. 1 shows a right clamp half 11 of a surgical clamp with a housing 15 and a first toothed rod 13, arranged in the housing 15, and a toothing 14. The first toothed rod 13 has a curvature in its lengthwise dimension, wherein the toothing 14 is oriented toward the midpoint of the curvature. An opposite curvature, wherein the toothing is oriented away from the midpoint of the curvature, is likewise possible.

"Right clamp half" means here, as illustrated by means of the curvature in the hook-shaped region of the right clamp half 11, the half of the surgical clamp that grasps the right side of a bone, as seen from the perspective of a patient (e.g., the patient's right side). The surface of the hook-shaped region facing the bone is provided with a structurization 12, more precisely, a tooth structure, which improves the hold of the right clamp half on the bone. The upper region of the right clamp half 11 is formed by a housing 15, which has an opening, indicated by the broken line, running through it in the direction of extension of the first toothed rod 13. In the embodiment depicted, the first toothed rod 13 forms a single piece with the right clamp half 11; but it is also possible to have a two-piece design where rod 13 is removable. In the configuration shown, the toothing 14 of the first toothed rod 13 points in the direction of the hook-shaped region of the right clamp half 11 and the first toothed rod 13 is arranged above the opening passing through the housing 15; but it would also be possible for the toothing 14 to point upward, if the first toothed rod 13 is arranged below the opening passing through the housing 15.

The toothing 14 is characterized in that the tooth flanks 16 pointing away from the right clamp half 11 rise more shallowly than the tooth flanks 17 pointing toward it. The tooth flanks 16, 17 belonging to each tooth furthermore run from the base of the tooth 18 to the tip of the tooth 19, obviously looking in the same direction, here, from upper right to lower left.

Figure 2:
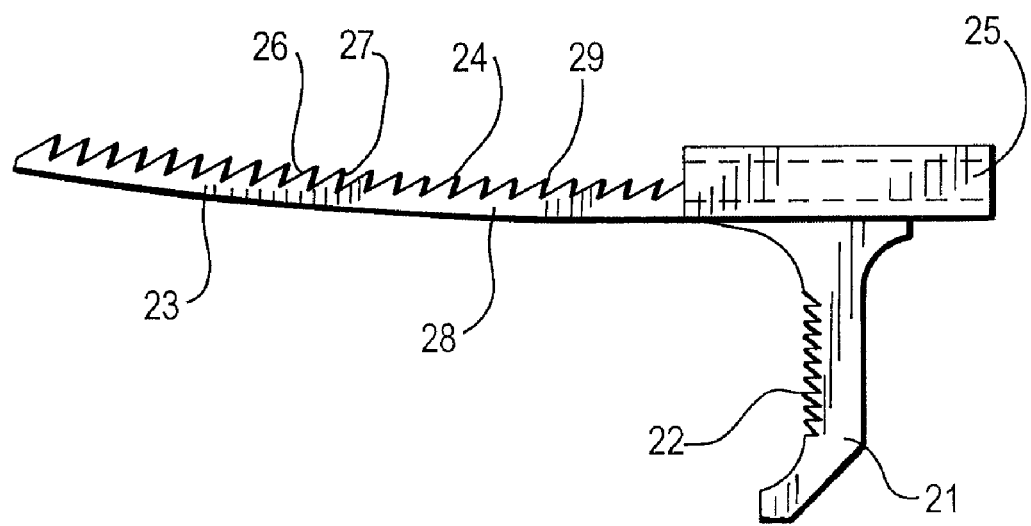
FIG. 2 is a side elevated view of a left clamp half and a second toothed rod of a clamp according to the invention.

FIG. 2 shows a left clamp half 21 of a surgical clamp with a housing 25 and a second toothed rod 23 arranged in the housing 25 with a toothing 24. The second toothed rod 23 has a curvature in the direction of its lengthwise dimension, and the toothing 24 is oriented to the midpoint of the curvature.

"Left clamp half" means, as illustrated by means of the curvature in the hook-shaped region of the left clamp half 21, the half of the surgical clamp which grasps the left side of a bone, as seen from the patient. The surface of the hook-shaped region facing the bone is provided with a structurization 22, more precisely a tooth structure, which improves the hold of the left clamp half 21 on the bone. The upper region of the left clamp half 21 is formed by a housing 25, which has an opening, indicated by the broken line, running through it in the direction of extension of the second toothed rod 23. In the embodiment depicted, the second toothed rod 23 forms a single piece with the right [sic!] clamp half 21; but it is also possible to have a two-piece design. In the configuration shown, the toothing 24 of the second toothed rod 23 points in the direction of the hook-shaped region of the left clamp half 21 and the second toothed rod 23 is arranged below the opening passing through the housing 25; but it would also be possible for the toothing 24 to point upward, if the second toothed rod 23 is arranged below the opening passing through the housing 25.

The toothing 24 is characterized in that the tooth flanks 26 pointing away from the left clamp half 21 rise more shallowly than the tooth flanks 27 pointing toward it. The tooth flanks 26, 27 belonging to each tooth furthermore run from the base of the tooth 28 to the tip of the tooth 29, obviously looking in the same direction, here, from lower left to upper right.

Figure 3:
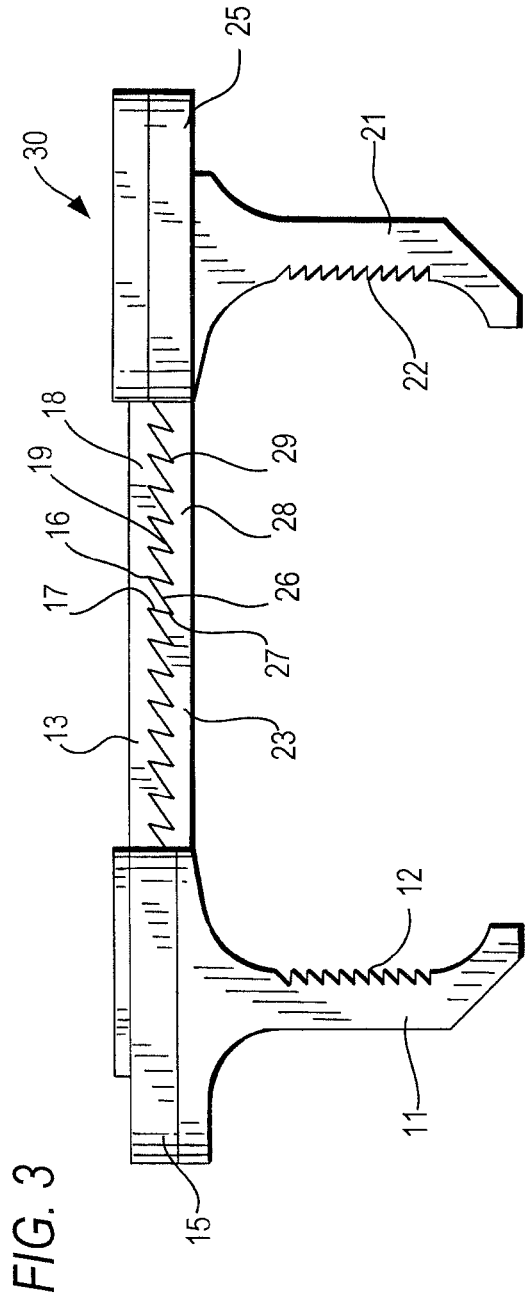
FIG. 3 is a side elevated view of an assembled clamp containing the components shown in FIGS. 1 and 2.

FIG. 3 shows a side view of a clamp 30 assembled from the components shown in FIGS. 1 and 2, with a right clamp half 11 with structurization 12 and housing 15, a first toothed rod 13 and a second toothed rod 23, as well as a left clamp half 21 with structurization 22 and housing 25. During an assembly, clamp 30 is put together by introducing the first toothed rod 13 into the opening passing through the housing 25 and at the same time introducing the second toothed rod 23 into the opening passing through the housing 15. Then the right clamp half 11 and the left clamp half 21 are moved toward each other under pressure until the halves of the breastbone from the hook-shaped regions of the right clamp half 11 and the left clamp half 21 are pressed against each other with the desired pressure. This can also occur only in a position where the toothed rods 13, 23 have already passed entirely through the openings into which they were introduced and have come out again on the other side. If such protruding toothed rods 13, 23 are a disturbance, they can be cut off after reaching the desired final position.

In other words, the clamp 30 must be configured so that it is possible to move the two clamp halves toward each other by pressing and/or pulling, whereas a movement in the opposite direction is impossible.

For this, the toothings 14, 24 of the first toothed rod 13 and the second toothed rod 23 must be configured so that they point toward each other, and the respective shallow tooth flanks 16, 26 of the toothings 14, 24 lie against each other, so that it is possible for the teeth to jump over each other when a certain pressure is applied, while the steep tooth flanks 17, 27 mesh with each other, so that a back movement is not possible, even when pulled strongly. Granted these conditions, it is also possible, for example, to use a pair of toothed rods 13, 23 whose toothings 14, 24 would project into the plane of the page or out from it, given the orientation of the first clamp half 11 and the second clamp half 21 as shown in FIG. 3.

Besides the orienting of the toothings 14, 24 and the adapting of their shape to each other, the curvature of the toothed rods 13, 23 oriented to each other plays an important role is providing the best possible hold of the surgical clamp 30. Namely, this ensures that the toothed rods 13, 23 after being introduced into the openings passing through the housing 15, 25 are braced against each other, so that the toothings 14, 24 are pressed against each other for at least a segment.

At the same time, of course, one must ensure that a movement of the right clamp half 11, as well as the left clamp half 22 relative to the toothed rods 13, 23 is no longer possible, at least in the end position of the surgical clamp 30. This is granted any way, for a single-piece design of the clamp halves and toothed rods 11 and 13, and 21 and 23; otherwise, this condition can be fulfilled by providing a mechanical stop. The clamped breastbone itself provides this function in the direction of movement of the clamp halves 11, 21 toward the breastbone; in the direction of movement of the clamps away from the breastbone, it is necessary to provide an appropriate stop on the toothed rods 13 and 23.

Figure 4:
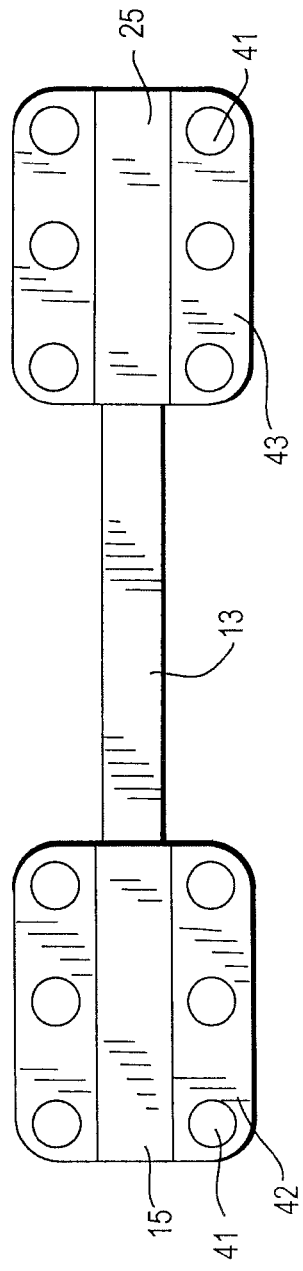
FIG. 4 is a top view of the assembled claim looking from the top downwardly in FIG. 3.

FIG. 4 shows a view of the clamp 30 in which the hook-shaped regions of the right clamp half 11 and the left clamp half 21 point into the plane of the page (e.g., a top view). Consequently, in this representation, only the housings 15, 25 and the top side of the first toothed rod 13 can be seen. In the embodiment of the surgical clamp shown in FIG. 4, a plate 42 is provided in addition on the housing 15 of the first clamp half 11 and a plate 43 on the housing 25 of the second clamp half 21, each of them having a plurality of lugs 41. These lugs make possible a further securing of the clamp by screwing it to the breastbone.

Another sample embodiment of the invented clamp is shown in FIG. 5 to 8. The same reference numbers are again used for the same parts, for sake of simplicity. In contrast with the sample embodiment in FIGS. 1-2, the right clamp half 11 and the left clamp half 21 now have first toothed rods 13 and second toothed rods 23 which are curved in directions opposite to the sample embodiment of FIGS. 1 and 2. As a further sample embodiment, the right clamp half 11 is distinctly smaller in cross section at its first toothed rod 13 than the toothed rod 23 of the left clamp half 23. To illustrate the different cross sections of the first toothed rod 13 and the second toothed rod 23, FIGS. 6 and 8 show section Y-Y of FIG. 5 and section X-X of FIG. 7, respectively.

It can be clearly seen in FIG. 6 that the cross section of the toothed rod 13 is smaller than the cross section of the toothed rod 23. In the sample embodiment of FIG. 6 it is proposed as assumed that the toothed rod 13 has a width A, being 4 mm for example, and a height B of 1 mm, e.g. The toothed rod 23 likewise has a width A of 4 mm, e.g., but a greater height B1 of 2.5 mm, e.g.

As a result of this difference in dimensioning of the cross sections of the toothed rods 13 and 23, one achieves the necessary stiffness, and at the same time an optimized spring action of the clamp, but the specific dimensions or measurements are not limiting thereto.

Basically, the ratio of the cross sections of the two toothed rods 13 and 23 to each other can be chosen depending upon the requirements having realized the invention. However, one should make sure that one of these toothed rods—the upper toothed rod 13 in the present sample embodiment—has a sufficient spring action by virtue of the small cross section. Adequate stiffness is provided by the thicker toothed rod 23, which in the present sample embodiment is arranged at the bottom when the clamp is assembled.

Figure 9A:
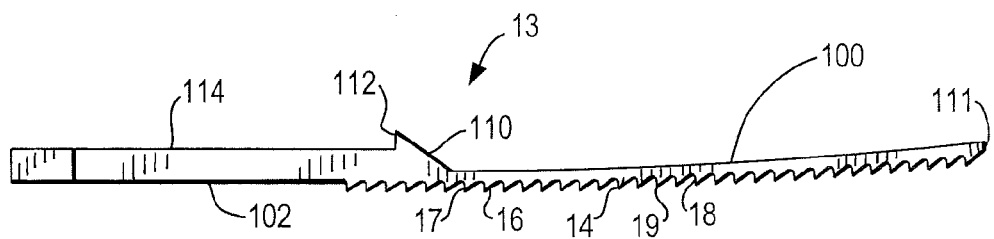
FIG. 9 is a combined figure of two views depicting a further embodiment of the present invention of a surgical clamp with a top plan view and a side elevational view of an alternative first toothed rod member having a broadened end region and improved opening and actuation features.
Figure 9B:
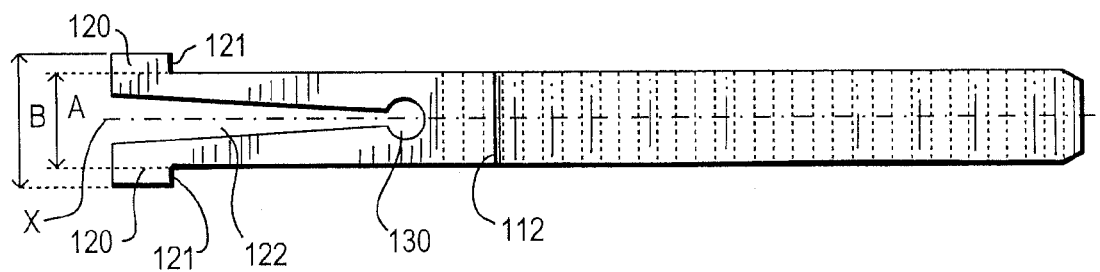

In conjunction with FIG. 9, a further sample embodiment of the surgical clamp is represented. It is assumed here that the clamp halves and the toothed rods have a two-piece design. This means that the first toothed rod of the first clamp half is shoved into the opening of the housing 15 from behind. The same holds for the second rod 23 (see FIG. 7 for this), which is likewise introduced from behind into the opening in the housing 25 of the left clamp half 21.

To enable a loosening of the two clamp halves 11, 21 which have been put together, it is possible to simply cut up the two toothed rods in the assembled clamp, using suitable cutting means, known to those of the surgical cutting arts.

The drawback to this is that the toothed rods of the clamp halves become destroyed in this way. To enable a simple loosening without destroying the clamp, FIG. 9 shows the toothed rod 13 of the right clamp half in modified form. The already familiar reference numbers stand for the same parts with the same meaning.

As can be seen from FIG. 9, the toothed rod 13 has been modified so that on the upper side 100 of the first toothed rod 13, roughly in the middle, an edge 110 is provided, running at a slant from the tip 111 of the first toothed rod 13, depicted at the right of FIG. 9, toward the rear, making an angle of around 45 degrees. Adjoining this slanting edge 110 is a recessed vertical edge 112, which then continues to run parallel to the lower side 102 of the first toothed rod 13 in a rear segment 114 of the first toothed rod 13. The vertical edge 112 serves as a stop when the toothed rod 13 is shoved into the opening in the housing 15 of the right clamp half 11.

Furthermore, the toothed rod 13 of FIG. 9 has a broadened region 120 in its rear segment 114 at the end away from the tip 111 of the toothed rod 13. This broadened region 120 is produced in that the outer contour of the toothed rod 13 has an edge 121 recessed preferably at a right angle, so that the width of the toothed rod 13 broadens from a first width A to a second width B. The recessed edges 121 serve as a stop when the toothed rod 113 is introduced into the opening in the housing 15 of the right clamp half 11, so that the toothed rod 13 upon reaching this recessed edge 121 cannot penetrate any further into the opening 15 of the right clamp half 11.

When this first toothed rod 13 is not engaging with the second toothed rod 23 of the left clamp half 21, not shown in FIG. 9, a deliberate loosening of the entire clamp is possible by compressing the rear segment 114 of the first toothed rod 13 from both sides of the broadened segment 120 in the direction of the center axis X. This compressing is possible because a preferably V-shaped slot has been fashioned in the toothed rod 13 in the rear segment 114 of the toothed rod 13. The slot starts at a round circular opening and broadens in the direction of the recessed edges 121 into a V shape. When the broadened region 120 of the toothed rod 13 is compressed, this broadened region 121 plus recessed edge 121 can be shoved through the opening in the housing 15, so that the entire clamp can be opened.

In the claims, means- or step-plus-function clauses are intended to cover the structures described or suggested herein as performing the recited function and not only structural equivalents but also equivalent structures. Thus, for example, although a nail, a screw, and a bolt may not be structural equivalents in that a nail relies on friction between a wooden part and a cylindrical surface, a screw's helical surface positively engages the wooden part, and a bolt's head and nut compress opposite sides of a wooden part, in the environment of fastening wooden parts, a nail, a screw, and a bolt may be readily understood by those skilled in the art as equivalent structures.

Having described at least one of the preferred embodiments of the present invention with reference to the accompanying drawings, it is to be understood that the invention is not limited to those precise embodiments, and that various changes, modifications, and adaptations may be effected therein by one skilled in the art without departing from the scope or spirit of the invention as defined in the appended claims.

LIST OF REFERENCE SYMBOLS

11 right clamp half
12 structurization
13 first toothed rod
14 toothing
15 housing
16 shallow flank of tooth profile
17 steep flank of tooth profile
18 base of tooth
19 tip of tooth
21 left clamp half
22 structurization
23 second toothed rod
24 toothing
25 housing
26 shallow flank of tooth profile
27 steep flank of tooth profile
28 base of tooth
29 tip of tooth
30 clamp, especially surgical clamp
41 lug
42 plate
43 plate
100 upper side of first toothed rod
102 lower side of first toothed rod
110 slanting edge
111 tips of the toothed rod
112 vertical edge
114 rear segment of first toothed rod
120 broadened region
121 recessed edge
122 V-shaped slot
130 round opening
X center axis of first toothed rod
A first width
B second width

The invention claimed is:

1. A surgical clamp, comprising:
a left clamp half,
a right clamp half,
a first toothed rod affixed on one end to the right clamp half,
a detent mechanism within the left clamp half engageable with the first toothed rod to secure the left clamp half at a distance from the right clamp half; and
characterized in that the detent mechanism engageable with the first toothed rod has a detent region extending at least from the left clamp half to the right clamp half,
wherein the detent mechanism engaging in the first toothed rod is a second toothed rod;

the left clamp half and the right clamp half are each provided with a respective housing;

the housings each having a continuous opening bounding a through passage into which at least one of the toothed rods can be introduced during a use thereof;

the width of the openings of each of the housings being adapted to the width of the respective toothed rods:

at least one plate having lugs is provided on at least one of the toothed rods or on the clamp halves. whereby the at least one plate enables affixing the clamp to an external bone member during the use;

a toothing of each respective toothed rod is respectively configured such that a plurality of flanks belonging to respective teeth of each said toothing run in the same direction relative to said toothing from the perspective of a base of the tooth to a tip of the tooth.

2. The surgical clamp, according to claim 1, wherein:
the first toothed rod and the second toothed rod are of substantially equal lengths.

3. The surgical clamp, according to claim 1, wherein:
the first toothed rod and the second toothed rod are of different lengths.

4. The surgical clamp, according to claim 1, wherein:
the right clamp half and the first of the toothed rods as well as the left clamp half and the second of the toothed rods are each of a two-piece design.

5. The surgical clamp, according to claim 1, wherein:
at least a portion of the surface of at least one of the left clamp half and the right clamp half positioned for contacting the external bone further comprise a friction enhancing structurization.

6. The surgical clamp, according to claim 1, wherein:
the teeth of each respective toothed rods are covered when the clamp is in said use.

7. The surgical clamp, according to claim 1, wherein:
at least one of the toothed rods has a semicircular profile.

8. A surgical clamp, comprising:
a left clamp half,
a right clamp half,
a first toothed rod affixed on one end to the right clamp half,
a detent mechanism within the left clamp half engageable with the first toothed rod to secure the left clamp half at a distance from the right clamp half; and
characterized in that the detent mechanism engageable with the first toothed rod has a detent region extending at least from the left clamp half to the right clamp half,
wherein the detent mechanism engaging in the first toothed rod is a second toothed rod;
the left clamp half and the right clamp half are each provided with a respective housing:
the housings each having a continuous opening bounding a through passage into which at least one of the toothed rods can be introduced during a use thereof;
the width of the openings of each of the housings being adapted to the width of the respective toothed rods:
at least one of the toothed rods has a curvature along its lengthwise dimension, wherein a toothing is directed at least one of toward a midpoint of the curvature and away from the midpoint of the curvature.

9. The surgical clamp, according to claim 8, wherein:
both the toothed rods have a curvature along their lengthwise dimension, wherein the toothing is directed at least one of toward a midpoint of the curvature and away from the midpoint of the curvature and the curvatures are opposite to each other.

10. The surgical clamp, according to claim 9, wherein:
the curvature of the first toothed rod and the curvature of the second toothed rod are each concave relative to a use position.

11. The surgical clamp, according to claim 9, wherein:
the curvature of the first toothed rod and the curvature of the second toothed rod are each convex relative to a use position.

12. The surgical clamp, according to claim 8, wherein:
each of the toothed rods includes a respective cross-section there through perpendicular to a length direction; and
each said cross-section is of a different size, with one cross-section being larger than the other and thereby defining a larger and a smaller cross-section.

13. The surgical clamp, according to claim 12, wherein:
at least a portion of the surface of at least one of the left clamp half and the right clamp half positioned for contacting the external bone further comprise a friction enhancing structurization;
the larger cross-section in a use condition of said clamp being spaced from the friction enhancing structurization more than a distance of the smaller cross-section.

14. The surgical clamp, according to claim 8, wherein:
the first toothed rod and the second toothed rod are of substantially equal lengths.

15. The surgical clamp, according to claim 8, wherein:
the first toothed rod and the second toothed rod are of different lengths.

16. The surgical clamp, according to claim 8, wherein:
the right clamp half and the first of the toothed rods as well as the left clamp half and the second of the toothed rods are each of a two-piece design.

17. The surgical clamp, according to claim 8, wherein:
at least a portion of the surface of at least one of the left clamp half and the right clamp half positioned for contacting the external bone further comprise a friction enhancing structurization.

18. A surgical clamp, comprising:
a left clamp half,
a right clamp half,
a first toothed rod affixed on one end to the right clamp half,
a detent mechanism within the left clamp half engageable with the first toothed rod to secure the left clamp half at a distance from the right clamp half; and
characterized in that the detent mechanism engageable with the first toothed rod has a detent region extending at least from the left clamp half to the right clamp half,
wherein the detent mechanism engaging in the first toothed rod is a second toothed rod;
the left clamp half and the right clamp half are each provided with a respective housing:
the housings each having a continuous opening bounding a through passage into which at least one of the toothed rods can be introduced during a use thereof;
the width of the openings of each of the housings being adapted to the width of the respective toothed rods:
at least one of the toothed rods further comprises a slot in a rear segment thereof; and
said slot facing away from a toothing of the at least one toothed rod.

19. The surgical clamp, according to claim 18, wherein:
the slot is V-shaped.

20. The surgical clamp, according to claim 18, wherein:
the first toothed rod and the second toothed rod are of substantially equal lengths.
21. The surgical clamp, according to claim 18, wherein:
the first toothed rod and the second toothed rod are of different lengths.
22. The surgical clamp, according to claim 18, wherein:
the right clamp half and the first of the toothed rods as well as the left clamp half and the second of the toothed rods are each of a two-piece design.

23. The surgical clamp, according to claim 18, wherein:
at least a portion of the surface of at least one of the left clamp half and the right clamp half positioned for contacting the external bone further comprise a friction enhancing structurization.
24. The surgical clamp, according to claim 8, wherein:
at least one of the toothed rods has a semicircular profile.

* * * * *

UNITED STATES PATENT AND TRADEMARK OFFICE
CERTIFICATE OF CORRECTION

PATENT NO. : 8,348,984 B2  
APPLICATION NO. : 12/261453  
DATED : January 8, 2013  
INVENTOR(S) : Rehm Page 1 of 1

It is certified that error appears in the above-identified patent and that said Letters Patent is hereby corrected as shown below:

On the title page item (73) Assignee: "Max Hauster Süeddeutsche Chirurgiemechanik GmbH" should be changed to -- "Max Hauser Süeddeutsche Chirurgiemechanik GmbH" --

Signed and Sealed this
Fifth Day of March, 2013

Teresa Stanek Rea
*Acting Director of the United States Patent and Trademark Office*